United States Patent [19]

Wissner et al.

[11] Patent Number: 4,762,935

[45] Date of Patent: Aug. 9, 1988

[54] PRECURSORS AND SYNTHESIS OF METHYL-9-OXO-11α,16-DIHYDROXY-16-VINYL-5-CIS-13-TRANS-PROSTADIENOATES

[75] Inventors: Allan Wissner, Ardsley; Kenneth E. Green, Suffern; Philip R. Hamann, Pearl River; Jeremy Levin, Spring Valley, all of N.Y.

[73] Assignee: American Cyanamid Company, Stamford, Conn.

[21] Appl. No.: 915,432

[22] Filed: Oct. 6, 1986

[51] Int. Cl.[4] .............................................. C07F 7/22

[52] U.S. Cl. .................................... 549/210; 549/422; 556/88; 556/112; 556/441; 560/121; 562/503; 568/595

[58] Field of Search ........................... 556/88; 549/210

[56] References Cited

PUBLICATIONS

Suzuki, et al., J. Am. Chem. Soc., 107, 3348, (1985).

Primary Examiner—Robert Gerstl
Attorney, Agent, or Firm—E. A. Conroy

[57] ABSTRACT

This disclosure describes novel compounds which are useful as precursors in the synthesis of 9-oxo-11α,16-dihydroxy-16-vinyl-5-cis-13-trans-prostadienoate esters which possess activity as hypotensive agents and/or as vasodilators.

1 Claim, No Drawings

PRECURSORS AND SYNTHESIS OF METHYL-9-OXO-11α,16-DIHYDROXY-16-VINYL-5-CIS-13-TRANS-PROSTADIENOATES

SUMMARY OF THE INVENTION

This invention relates to novel compounds which are advantageously used as precursors in the synthesis of methyl-9-oxo-11α,16-dihydroxy-16-vinyl-5-cis-13-trans-prostadienoates, their congeners and racemic mixtures thereof.

These prostadienoates are pharmacologically active as hypotensive agents and/or vasodilators. One of such prostadienoates having vasodilator and hypotensive activity, namely methyl-9-oxo-11α,16-dihydroxy-16-vinylprosta-5-cis-13-trans-dienoate, having the structure

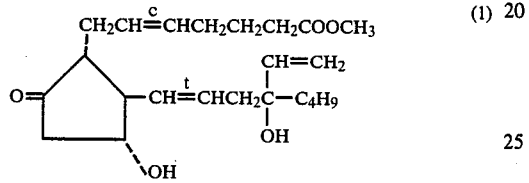

has been described in U.S. Pat. Nos. 4,198,521 and 4,311,707 and by J. E. Birnbaum, et al., J. Med. Chem., 25, 492 (1982).

This invention also relates to novel processes of synthesizing new compounds which are precursors to the pharmacologically active compounds cited above.

The novel compounds and processes of this invention provide a simpler, more rapid and economical means of producing pharmacologically active prostadienoates of greatly increased purity as compared to the compounds and processes used heretofore.

DETAILED DESCRIPTION OF THE INVENTION

Methyl-9-oxo-11α,16-dihydroxy-16-vinyl-5-cis-13-trans-prostadienoate (1) can be prepared as the individual 16R and 16S diastereomers. Each of these diastereomers can be prepared as a racemate or as the individual optical isomers. The novel precursor compounds of this invention, as well as the novel synthetic methods used to accomplish the preparation are described hereinbelow in flowcharts A through E.

In accordance with Flowchart A, the reaction of the nitrile (2) with hydrogen chloride and a $C_1$-$C_5$ alcohol ($R_1$=$C_1$-$C_5$) in ether, followed by treatment of the resulting imidinium salt with the same $C_1$-$C_5$ alcohol in an inert solvent such as hexane, gives the ortho ester (3). Metalation of (3) with n-butyl lithium or sodium amide, followed by the addition of dry formaldehyde gas gives the alcohol (4). Hydrolysis of (4) with dilute acid gives the ester (5). Reduction of (5) with hydrogen and Lindlar catalyst gives the cis olefin (6) which, on reaction with phosphorous tribromide in an inert solvent such as hexane, gives the allyl bromide (7). The reaction of (7) with an excess of sodium iodide in an inert solvent such as acetone gives the allyl iodide (8).

Compounds (7) and (8) have been prepared previously by a different method, not involving the novel intermediate (4) [R. E. Donaldson, et al., J. Org. Chem., 48, 2167 (1983)]. The method of the present invention furnishes (8) in higher overall yield and represents an improved preparation.

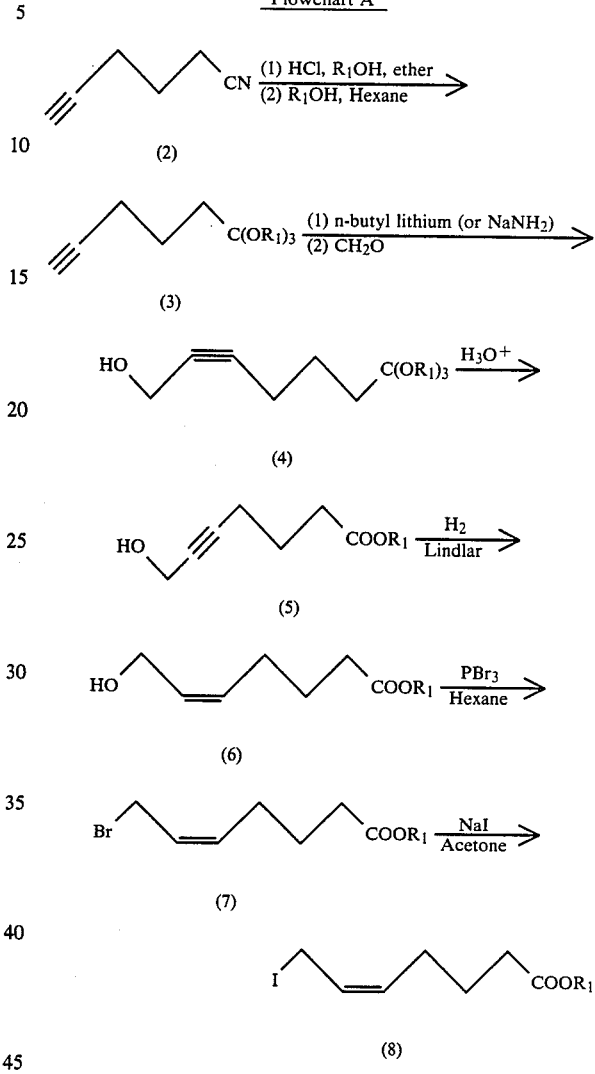

The desired prostaglandins represented by formula (14) can be prepared from (8) as shown hereinbelow in Flowchart B.

In accordance with Flowchart B, the cyclopentenone (9), wherein P represents an acid labile hydroxy protecting group such as tetrahydropyranyl or $C_1$-$C_6$ trialkylsilyl, is reacted with the vinyl cuprate reagent represented by formula (10), wherein the radical —Cu—L— represents a copper atom coordinated with one or more alkynyl, vinyl, or trialkylphosphine ligands (R'=$C_1$-$C_6$), at low temperature (−100° C. to −20° C.) in an ether like solvent, to give the copper enolate represented by formula (11). Transmetalation of (11) with a triaryl tin chloride represented by formula (12), wherein R'' is a phenyl ring, or a phenyl ring optionally substituted with $C_1$-$C_5$ alkyl groups, gives the triaryl tin enol ether represented by formula (13). The alkylation of (13) with an excess of the allyl iodide (8) in the presence of an activator such as hexamethylphosphoramide (HMPA), followed by removal of the protecting groups with dilute acid, or optionally in the cases where P is a silyl group with hydrogen fluoride-pyridine in tetrahydrofuran, gives the desired 16-vinyl prostaglandins represented by formula (14).

and M. Suzuki, et al., J. Amer. Chem. Soc., 107, 3348 (1985).

Flowchart B

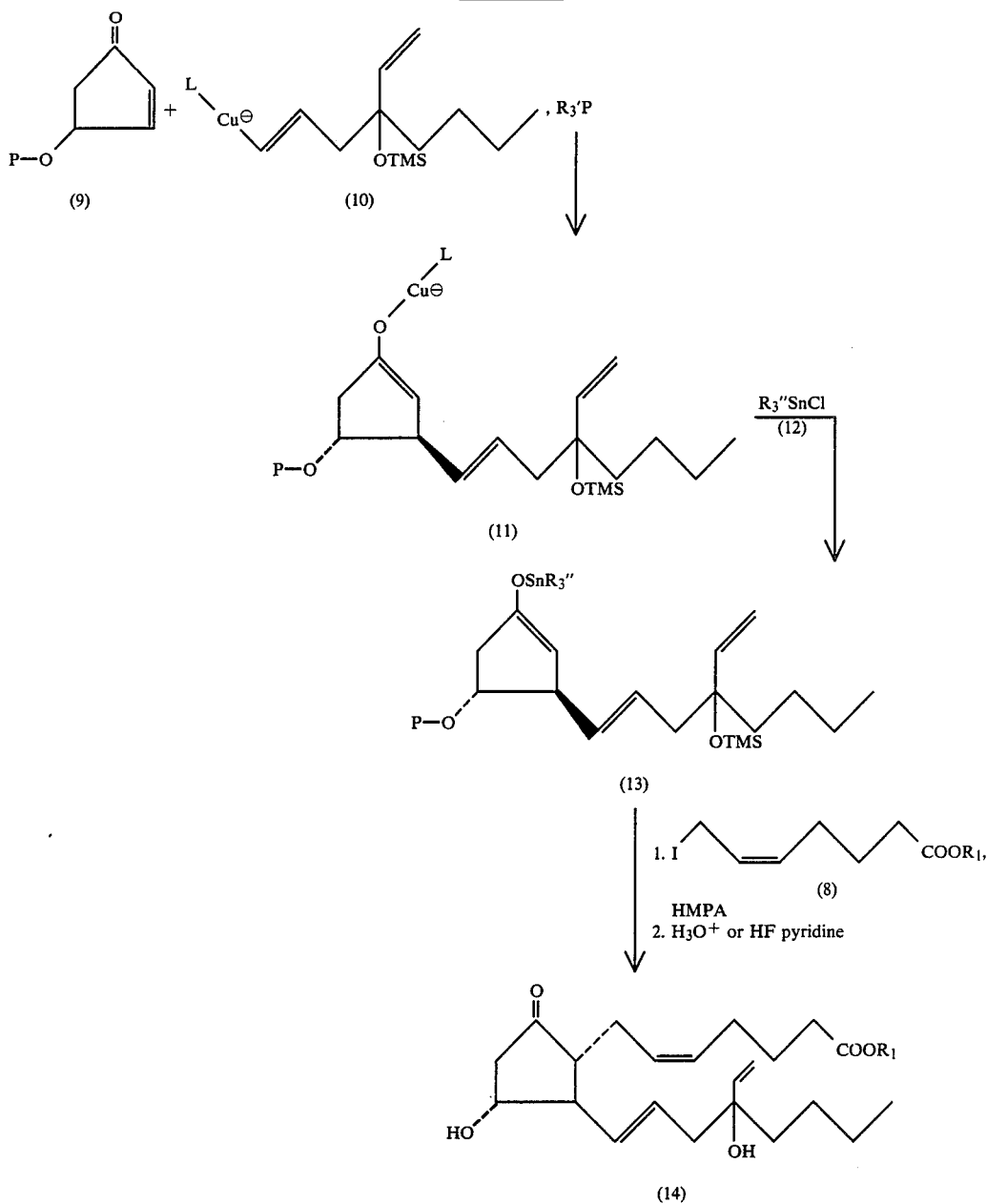

If the starting cyclopentenone (9) is racemic, the resulting intermediates and final products (11), (13) and (14) are each obtained as a mixture of diastereomers, each of which is racemic. In the case of (14) the two diastereomers can be separated by HPLC.

If the starting cyclopentenone (9) is optically active the resulting intermediates and final products (11), (13) and (14) are each obtained as a mixture of diastereomers, each of which is optically active. In the case of (14) the two diastereomers can be separated by HPLC furnishing the compounds in optically active form.

The preparation of (9) in both its racemic and optically active forms has been previously described by R. Davis and K. G. Untch, J. Org. Chem., 44, 3755 (1979)

When compared to previous methods [J. Med. Chem., 25, 492 (1982)], a major advantage of the above embodiment of the present invention is the high degree of stereoselectivity obtained with respect to the double bond between carbon atoms 5 and 6. In the previous methods the double bond between carbon atoms 5 and 6 is formed via a Wittig reaction; as a consequence of this, the product prostaglandins are contaminated with significant amounts of the two 5-trans isomers. The separation of the two 5-cis diastereomers from the two 5-trans diastereomers is extremely difficult and can only be accomplished on a small scale using analytical high pressure chromatography. In the present method, the double bond between carbon atoms 5 and 6 is not formed via a Wittig reaction, but is formed by a partial hydrogenation of the acetylene bond of intermediate (5). This reaction is highly stereoselective; the older methods produce the prostaglandins (14) containing up to 300% more of the 5-trans isomer impurities.

Alternative methods to prepare the prostaglandins represented by formula (14) are described hereinbelow in flowcharts C, D and E, wherein P, $R_1$ and R" are as hereinabove defined and X is a sulfur or selenium atom.

As described in Flowchart C, the reaction of cyclopentenone (9) with the reagent (15) (prepared by mixing one equivalent of trimethyl aluminum with thiophenol or phenyl selenol) followed by the addition of an alkynyl aldehyde (16) at low temperature in an inert solvent such as methylene chloride or tetrahydrofuran gives, after aqueous workup, the compounds represented by formula (17) as a mixture of diastereomers. Dehydration of (17) with methylsulfonyl chloride and pyridine gives the conjugated compound (18). Reduction of (18) with a trialkyl tin hydride in an inert solvent such as toluene using a radical initiator such as azobisisobutyronitrile (AIBN), or reduction with zinc in a mixture of acetic acid and isopropanol furnishes the cyclopentenones represented by formula (19).

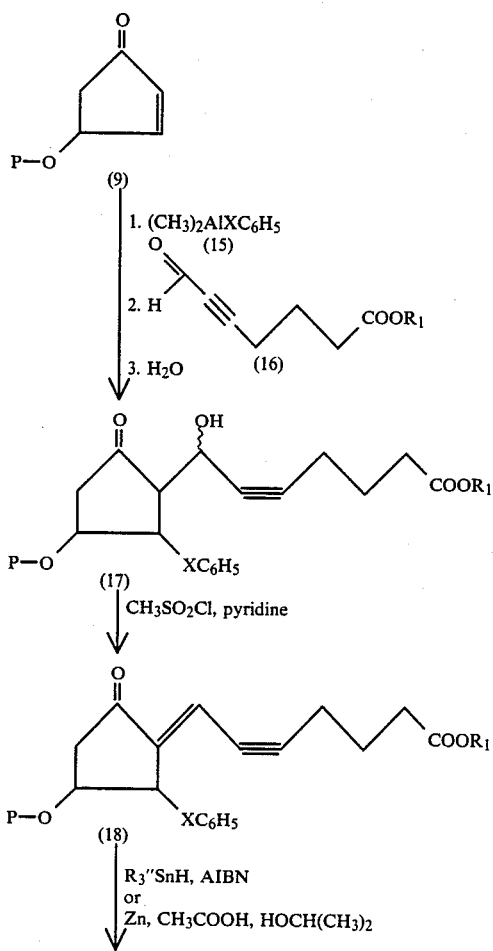

The conversion of the intermediate (19) to the prostaglandins represented by formula (14) is described hereinbelow in Flowchart D.

In accordance with Flowchart D, the partial catalytic hydrogenation of the triple bond in the compound (19) is preferably carried out with a poisoned palladium catalyst, or its equivalent, in a hydrocarbon solvent at $-10°$ to $+25°$ C. under one atmosphere of hydrogen. The preferred catalyst is palladium on calcium carbonate, lead-poisoned (Lindlar catalyst).

The product, cis-olefin (20), wherein P is trimethylsilyl and $R_1$ is methyl, is a known intermediate for the preparation of the useful prostadienoate ester of formula (14). The requisite transformations, which eventually provide the product (14) are shown in Flowchart D and are described in J. Med. Chem., 25, 492 (1982).

A major advantage of the above embodiment of the present invention is the high degree of stereoselection in the conversion of the acetylene group to a cis-olefin group through the agency of controlled partial catalytic hydrogenation.

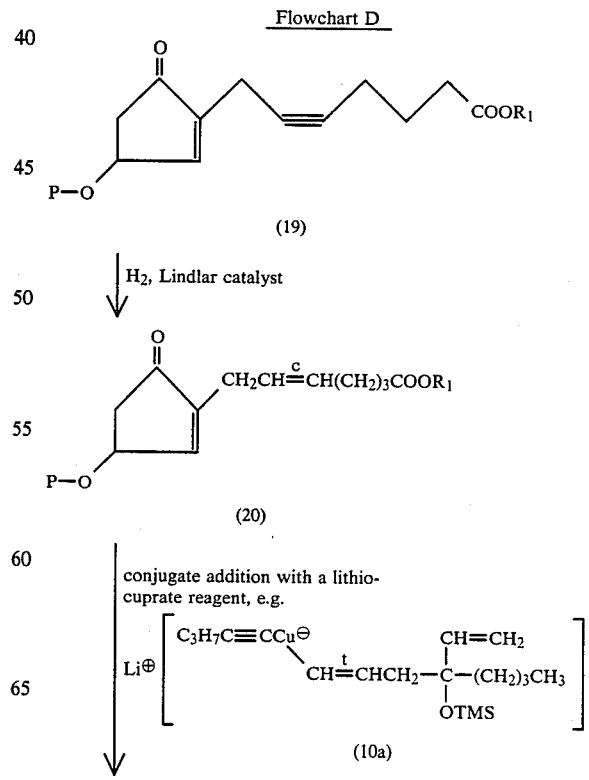

-continued
Flowchart D

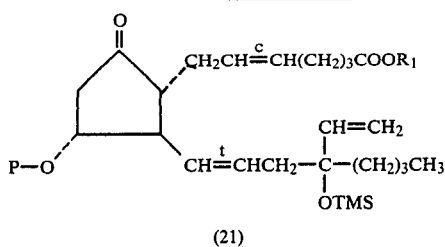
(21)

↓ hydrolysis of protecting groups

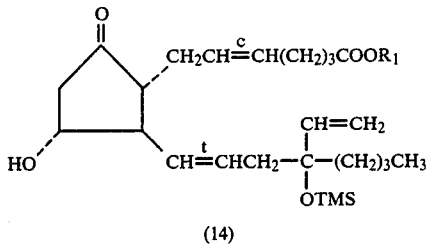
(14)

An alternative method for the preparation of prostadienoate esters such as (1) is shown in Flowchart E, wherein P and $R_1$ are as hereinabove defined.

In accordance with Flowchart E, the blocked cyclopentenone (19), prepared as described in Flowchart C, is reacted with a lithio-cuprate reagent (10a). The resulting blocked prostenynoate ester (22) is subjected to mild acid catalized hydrolysis of the protecting groups. The preferred conditions employ acetic acid in aqueous tetrahydrofuran at 25°-40° C., or hydrogen fluoride and pyridine in tetrahydrofuran. The resulting acetylenic diol (23) is subjected to partial catalytic hydrogenation to provide the useful prostadienoate esters (14). The preferred conditions employ a hydrocarbon solvent at 25°-40° C. under one atmosphere of hydrogen. A useful catalyst is palladium on calcium carbonate, lead-poisoned (Lindlar catalyst).

The method described hereinabove and outlined in Flowchart E furnishes the prostaglandin products (14) with a higher degree of stereoselectivity with respect to the $C_5-C_6$ double bond in comparison to previous methods.

If the starting cyclopentenone (9) is racemic, the resulting intermediates (17–23) and final products (14) are each obtained as a mixture of diastereomers, each of which is racemic. In the case of (14) the two diastereomers can be separated by HPLC.

If the starting cyclopentenone (9) is optically active, the resulting intermediates (17–23) and final products (14) are each obtained as a mixture of diastereomers, each of which is optically active. In the case of (14), the two diastereomers can be separated by HPLC furnishing the compounds in optically active form.

The preparation of (9) in both its racemic and optically active forms has been described in the references cited hereinabove.

Flowchart E

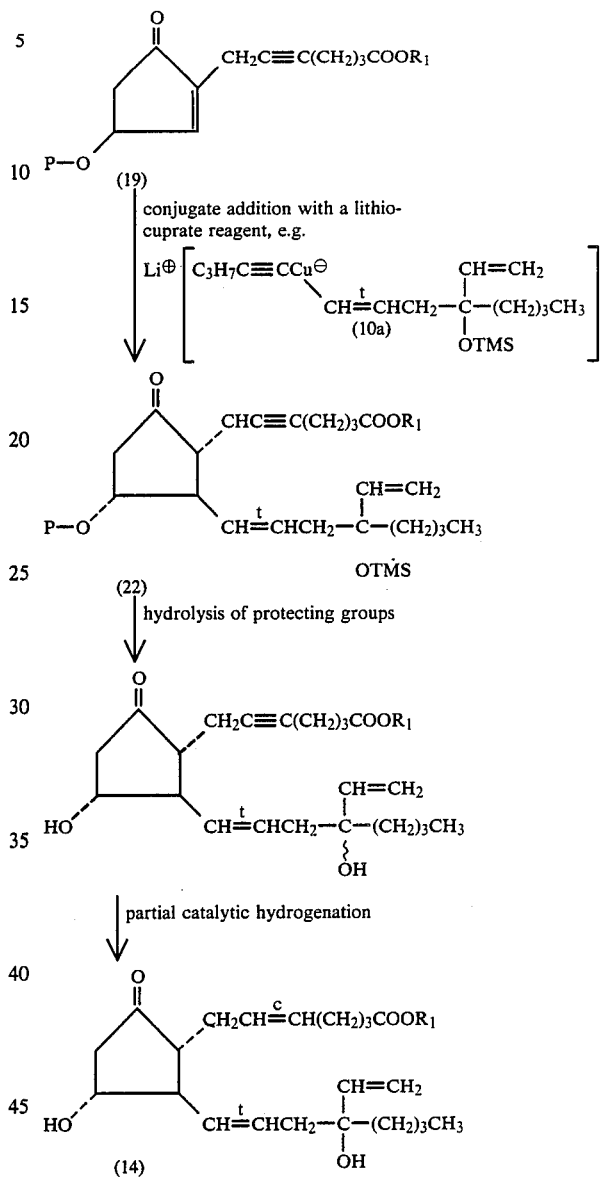

The invention will be described in detail in conjunction with the following non-limiting examples.

EXAMPLE 1

6,6,6-Trimethoxy-1-hexyne

To a solution of 100 g of 5-cyano-1-pentyne in 500 ml of dry ether, under nitrogen atmosphere, was added 44.2 ml of anhydrous methanol. After cooling to 0° C., dry gaseous hydrogen chloride was passed into the solution through a fritted gas tube. After TLC (20% ethyl acetate hexanes) indicated almost complete consumption of the starting material, another 22.1 ml of anhydrous methanol was added. The addition of gaseous hydrogen chloride was continued until the solution was saturated. The reaction mixture was diluted with hexanes, then stored overnight in a freezer. Since crystals were not produced, the mixture was stripped at reduced pressure. The resultant solid was pumped under high vacuum overnight, then suspended in 500 ml of hexanes under nitrogen and 120 ml of anhydrous methanol added. This mixture was stirred vigorously for 60 hours, then filtered. The filtrate was concentrated, redissolved in hexanes, refiltered, stripped and distilled rapidly on a kugelrohr (approximately 0.15 Torr, 60° C.), giving 160 g of the desired compound. NMR: 3.20 ppm (9H, s, OMe), 2.20 ppm (2H, td, 7 Hz, 2 Hz, (C—CH$_2$), 1.95 ppm (1H, d, 2 Hz, CCH), 1.95–1.35 ppm (4H, m, CH$_2$CH$_2$).

EXAMPLE 2

8-Hydroxy-5-heptynoic acid, methyl ester

To a solution of 60 g of 6,6,6-trimethoxy-1-hexyne in 1000 ml of dry tetrahydrofuran, under nitrogen at −15° C., was added 74 ml of 5.53M n-butyl lithium. A 20 g portion of gaseous formaldehyde, (prepared from 20 g of paraformaldehyde), was then passed over the solution in a slow stream of nitrogen. The reaction was quenched with 10% aqueous hydrochloric acid until acidic to litmus, then diluted with brine. After 1 hour, solid sodium bicarbonate was added until no more gas was evolved. The organic phase was separated and saved. The aqueous phase was extracted with an equal volume of ethyl acetate. The organic phases were combined, dried, concentrated and quickly distilled by kugelrohr (approximately 0.1 Torr, 90° C.), giving 48.8 g of the desired compound. NMR: 4.25 ppm (2H, br s, OCH$_2$), 3.75 ppm (variable, 1H, br s, OH), 3.60 ppm (3H, s, OMe), 2.40 ppm (2H, t, 7 Hz, O≡CCH$_2$), 2.30 ppm (2H, m, CCH$_2$), 1.80 ppm (2H, q, CH$_2$).

EXAMPLE 3

8-Hydroxy-5-heptynoic acid, trimethyl orthoester

This compound may be isolated by quenching the formaldehyde reaction in Example 2 with saturated aqueous ammonium chloride, saturating with sodium chloride and extracting with ethyl acetate. Attempted distillation of the crude product leads to decomposition, but an analytical sample may be obtained by chromatography of a portion of the impure distillate on silica gel in the presence of triethylamine (1%, 10–40% ethyl acetate/hexanes). NMR: 4.15 ppm (2H, t, 1 Hz, OCH$_2$), 3.20 ppm (9H, s, OMe), 2.65 ppm (1H, br s, OH), 2.30 ppm (2H, m, CCH$_2$), 2.0–1.4 ppm (4H, m, CH$_2$CH$_2$).

EXAMPLE 4 cis-7-Hydroxy-5-heptenoic acid, methyl ester

To a mixture of 8-hydroxy-5-heptynoic acid, methyl ester and 40 ml of hexanes was added 7.2 ml of quinoline (synthetic) and 750 mg of Lindlar catalyst. The reaction flask was purged with hydrogen and then the reaction mixture was stirred vigorously under one atmosphere of hydrogen (supplied via a gas balloon) for 24 hours. The reaction was worked up by adding 10% hydrochloric acid and brine and extracting twice with ethyl acetate. The combined organic layers were washed once with saturated aqueous bicarbonate, which was subsequently back-extracted once with ethyl acetate. The ethyl acetate mixtures were dried and concentrated. The crude product was purified by dissolution in 500 ml of water and washing with hexanes to remove nonpolar impurities. The hexane layer was back-extracted once with water, and the aqueous phases were saturated with sodium chloride and extracted twice with ethyl acetate. Drying and concentration gave 20.7 g of the desired compound. NMR: 5.75–5.3 ppm (2H, m, olefins), 4.15 ppm (1H, br s, OH), 4.1 ppm (2H, br d, 6 Hz, OCH$_2$), 3.65 ppm (3H, s, OMe), 2.55–1.95 (4H, m, CH$_2$—CH$_2$), 1.75 ppm (2H, q, 7 Hz, CH$_2$).

EXAMPLE 5 cis-7-Bromo-5-heptenoic acid, methyl ester

To 23.7 g of cis-7-hydroxy-5-heptenoic acid, methyl ester and 150 ml of hexanes under nitrogen at 0° C. was added dropwise, 7.05 ml of phosphorous tribromide. After 2 hours the reaction was quenched with ice, diluted with hexanes, washed once with water and once with saturated aqueous bicarbonate, dried and stripped at reduced pressure. The crude product was dissolved in ether and filtered through a plug of silica gel. Removal of the ether at reduced pressure gave 31.4 g of the desired compound. NMR: 5.95–5.35 ppm (2H, m, olefins), 3.95 ppm (2H, d, 7 Hz, BrCH$_2$), 3.65 ppm (3H, s, OMe), 2.45–2.05 ppm (4H, m, CH$_2$—CH$_2$), 1.8 ppm (2H, q, 7 Hz, CH$_2$).

EXAMPLE 6 cis-7-Iodo-5-heptenoic acid, methyl ester

To a solution of 31.4 g of cis-7-bromo-5-heptenoic acid, methyl ester in 260 ml of acetone, containing a trace of sodium carbonate was added a solution of 24.7 g of sodium iodide in 260 ml of acetone. A precipitate formed immediately. After 2 minutes, the solution was diluted with 850 ml of ether and filtered. A trace of sodium carbonate was added to the filtrate which was then stripped, redissolved in ether, refiltered, sodium carbonate added and the filtrate stripped, giving 37.9 g of light sensitive product. This product was stored in the cold as a 1M solution in either ether or tetrahydrofuran containing a trace of sodium carbonate and protected from the light. NMR: 5.95–5.2 ppm (2H, m, olefins), 3.85 ppm (2H, d, 7 Hz, ICH$_2$), 3.65 ppm (3H, s, OMe), 2.45–2.0 ppm (4H, m, CH$_2$—CH$_2$), 1.8 ppm (2H, q, 7 Hz, CH$_2$).

EXAMPLE 7

[3R-[3α(E),4β]]-4-[[(1,1-Dimethylethyl)dimethylsilyl]oxy]-3-[4-ethenyl-4-[(trimethylsilyl)oxy]-1-octenyl]-1-cyclopenten-1-ol, copper enolate To a solution of 242.1 mg of 1-E-tri-n-butylstannyl-4-trimethylsilyloxy-4-vinyl-1-octene in 1 ml of tetrahydrofuran at −78° C., under an argon atmosphere, was added dropwise, 0.19 ml of a 2.5M solution of n-butyl lithium in hexanes. The solution was warmed to −40° C. over a period of 1 hour and then recooled to −78° C. A homogeneous solution of 61.34 mg of copper pentyne and 0.26 ml of tri-n-butyl phosphine in 5 ml of diethyl ether was added dropwise. After stirring for 1 hour at −78° C., a solution of 100 mg of 4-[[(1,1-dimethylethyl)dimethylsilyl]oxy]-2-cyclopenten-1-one in 0.2 ml of tetrahydrofuran was added and stirring continued for 30 minutes to produce a −78° C. solution of the desired compound.

EXAMPLE 8

[3R-[3α(E),4β]]-4-[[(Dimethylethyl)dimethylsilyl]oxy]-3-[4-ethenyl-4-[(trimethylsilyl)oxy]-1-octenyl]-1-cyclopenten-1-ol, triphenyltin derivative A solution of 181.4 mg of chlorotriphenyltin in 0.2 ml of tetrahydrofuran was added to the final solution from Example 7. Stirring for 10 minutes produced a −78° C. solution of the desired compound.

EXAMPLE 9

Methyl-9-oxo-11α,16-dihydroxy-16-vinyl-prosta-5-cis-13-trans-dienoate

A 1M solution of cis-7-iodo-5-heptenoic acid, methyl ester in tetrahydrofuran was added to the −78° C. final solution from Example 8. After warming to −20° C. and stirring for 15 hours, the solution was recooled to −78° C. and quenched with saturated aqueous ammonium chloride. The mixture ws warmed to room temperature, then ether and water were added. The ether layer was separated, washed with brine, dried and concentrated in vacuo. The residue was dissolved in 5 ml of tetrahydrofuran and subjected to the action of hydrogen fluoride-pyridine (in the form of a solution prepared from mixing 6.5 g of 70% hydrogen fluoride in pyridine, 15.5 ml of pyridine and 50 ml of tetrahydrofuran). After stirring at room temperature for 2 hours, the solution was poured into saturated aqueous sodium bicarbonate and extracted with ether. The ether layer was washed with brine, dried and concentrated in vacuo. Purification of the residue via flash chromatography on silica gel, using the solvent system ethyl acetate:petroleum ether (60:40) gave 27.7 mg of the desired compound.

EXAMPLE 10

7-[3-[[(1,1-Dimethylethyl)dimethylsilyl]oxy]-5-oxo-2-(phenylthio)cyclopentyl]-7-hydroxy-5-heptynoic acid, methyl ester To a solution of 8.08 ml of a 0.7M solution of dimethyl aluminum benzene thiolate at −78° C. was added a solution of 1 g of 4-[[(1,1-dimethylethyl)dimethylsilyl]oxy]-2-cyclopenten-1-one in 4.8 ml of dichloromethane. The reaction mixture was stirred at −78° C. for 20 minutes and then diluted with 24 ml of dry tetrahydrofuran. After recooling to −78° C., a solution of 0.8 g of 7-oxo-5-heptynoic acid, methyl ester in 4.8 ml of dry tetrahydrofuran was added dropwise, over 5 minutes. The reaction was stirred at −78° C. for an additional 30 minutes and then quenched by pouring it into a rapidly stirred mixture of 200 ml of saturated ammonium chloride solution and 40 ml of ethyl acetate. The organic layer was separated, washed with water and brine, dried, concentrated in vacuo and this residue used in Example 11.

EXAMPLE 11

7-[3-[[(1,1-Dimethylethyl)dimethylsilyl]oxy]-5-oxo-2-(phenylthio)cyclopentylidene], methyl ester To a solution of the crude ester from Example 11 in 20 ml of dry pyridine, cooled to 0° C., was added dropwise 1.5 ml (2.22 g) of mesyl chloride. The reaction mixture was stirred at 0° C. for 3 hours, then allowed to warm to room temperature and diluted with 150 ml of water. The resulting suspension was extracted with chloroform and the combined organic extracts were washed with water and brine, dried and concentrated in vacuo. Flash chromatography of the residue on silica gel, using the system ethyl acetate:hexane (1:10) gave 1.71 g of the desired compound as a pale yellow oil. 'H NMR: (CDCl₃, 300 MHz), 7.62 (m, 2H), 7.45 (m, 3H), 6.72 (m, 1H), 4.49 (s, 1H), 4.45 (d, 1H, J=4.77 Hz), 3.77 (s, 3H), 2.99 (dd, 1H, J=4.78 Hz, 17.97 Hz), 2.63 (m, 4H), 2.39 (dd, 1H, J=1.86, 17.8 Hz), 2.02 (m, 2H), 0.89 (s, 9H), 0.12 (s 6H); IR (solution) 2210, 1740, 1720, 1615, 1070 cm⁻¹; MS (EI) m/e 401, 255, 155.

EXAMPLE 12

7-[3-[[(1,1-Dimethylethyl)dimethylsilyl]oxy]-5-oxo-1-cyclopenten-1-yl], methyl ester To a solution of 0.2 g of 7-[3-[[(1,1-dimethylethyl)dimethylsilyl]oxy]-5-oxo-2-(phenylthio)cyclopentylidene], methyl ester in 20 ml of isopropanol was added 62 μl of acetic acid and 0.285 g of zinc dust. The suspension was stirred at room temperature for 24 hours, then filtered through a pad of diatomaceous earth which was washed with 125 ml of ethyl acetate. The filtrate and wash were combined and washed with saturated sodium bicarbonate solution, water and brine, dried, filtered and concentrated in vacuo. Preparative TLC, using the system hexane:ethyl acetate (15:1), gave 0.077 g of the desired compound as a pale yellow oil. 'H NMR (CDCl₃, 300 MHz), 7.30 (m, 1H), 4.91 (m, 1H), 3.68 (s, 3H), 3.04 (m, 2H), 2.79 (dd, 1H, J=5.83, 18.29 Hz), 2.45 (t, 1H, J=7.40 Hz), 2.27 (m, 3H), 1.84 (m, 2H), 0.92 (s, 9H), 0.14 (s, H), 0.13 (s, 3H); IR (solution) 2210, 1740, 1720, 1640, 1620, 1085 cm⁻¹; MS (EI) m/e 319, 253, 219.

We claim:

1. A compound in optically active or racemic form selected from those of the formula:

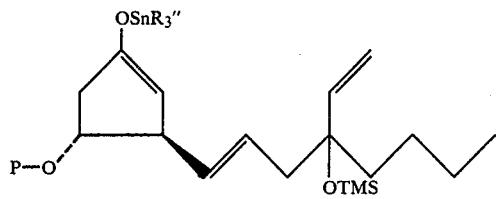

wherein P is tetrahydropyranyl or trialkylsilyl ($C_1$ to $C_6$ straight or branched chain) and R" is a phenyl ring or a phenyl ring optionally substituted with one or more $C_1$ to $C_5$ alkyl groups.

* * * * *